United States Patent
Hakki et al.

[11] Patent Number: 5,749,833
[45] Date of Patent: May 12, 1998

[54] COMBINED ECHO-ELECTROCARDIOGRAPHIC PROBE

[76] Inventors: A-Hamid Hakki; Said L Hakky, both of 8547 Merrimoor Blvd., E., Largo, Fla. 34647-3145

[21] Appl. No.: 515,315

[22] Filed: Aug. 15, 1995

[51] Int. Cl.$^6$ .............. A61R 5/042; A61R 8/12; A61B 8/12
[52] U.S. Cl. .............. 600/380; 600/462
[58] Field of Search .............. 128/642, 662.06; 607/124; 600/380, 462, 466

[56] References Cited

U.S. PATENT DOCUMENTS

| | | | |
|---|---|---|---|
| 4,319,580 | 3/1982 | Colley et al. | 128/662.06 |
| 4,706,681 | 11/1987 | Breyer et al. | 128/642 |
| 5,178,149 | 1/1993 | Imburgia et al. | 602/124 |
| 5,385,148 | 1/1995 | Lesh et al. | 128/662.06 |
| 5,630,837 | 5/1997 | Crowley | 128/662.06 |

*Primary Examiner*—Lee S. Cohen
*Attorney, Agent, or Firm*—John Lezdey

[57] ABSTRACT

An esophageal probe comprising in combination EKG electrodes and ECHO electrodes selectively spaced from each other for monitoring or pacing an organ at a single location which allows for more controlled stimulation of the selected organ and to provide more accurate diagnostic data.

7 Claims, 1 Drawing Sheet

COMBINED ECHO-ELECTROCARDIOGRAPHIC PROBE

BACKGROUND OF THE INVENTION

1. Field of the Invention

The invention relates to medical electrodes, more particularly to a combined echocardiographic and electrocardiographic esophageal probe.

2. Description of the Prior Art

It has long been known that a way to determine the presence and extent of coronary-disease (particularly coronary artery disease) is to monitor the ventricular wall motion of the heart operating at higher beat levels. Techniques to produce a sonogram or echocardiogram of the ventricular wall motion are known, and usually involve the use of a transthoracic transducer placed on the outside of the patient's chest in vicinity to the heart to visualize heart wall motion.

At present, in addition to the unpopular (and relatively unsafe) technique of a temporary pacing by means of an intravenous pacing wire implanted in contact with the heart (i.e., the i-v pacemaker), the art has developed two general types of diagnostic tests for patients who cannot be adequately stress tested to permit accurate assessment of coronary disease. First, there is the "pill electrode" type of device, as illustrated in U.S. Pat. No. 4,817,611, whereby the patient is induced to swallow a device which may be used to artificially stimulate (i.e., pace) the heart to higher activity. A second technique is to stress the heart pharmacologically, usually Dipyridamole. In both situations, the stressed heart's activity is then monitored by radionuclide imaging enhanced by thallium doping. The pharmacological technique has the drawback of possible irreversible medicinal side effects. The "pill electrode" is very uncomfortable to the patient, and the echocardiographic imaging modality associated with the pill electrode (i.e., transthoracic echocardiography) is often unsatisfactory.

Electrode probes for inserting into a body to record electrical signals from and to stimulate the heart are generally known in the prior art. Such probes are inserted into the body past the pharynx and into the esophagus or trachea into close proximity to the heart. Before the present invention an assortment of esophageal probes have been proposed for detecting sounds at a single location on the probe. However, the nature of the sounds depends upon the location. In the esophagus, the lung sounds of the patient are predominant. Thus, prior art probes do not readily provide separate heart and lung sounds from the patient.

Such probes may also be used either for diagnosis or for therapeutic applications. For diagnosis, the heart can be monitored, and for therapeutic purposes, an electrical signal may be applied to the heart via the probe. Techniques to produce a sonogram or echocardiogram of the ventricular wall motion are known and usually involve the use of a transthoracic transducer placed on the outside of the patient's chest in the vicinity of the heart. The technique described above may be more efficient if the esophageal electrode is positioned as close to the ventricle of the heart as possible. The closer the electrode is to the ventricle the less electrical energy is needed to perform the pacing or defibrillating functions, and the more accurate are the intended results. Esophageal probes are capable of being positioned closer to the heart compared to the other devices, since the esophagus lays against the heart in the vicinity of the left atrium. Since the transducer's sonic output is in close proximity to the heart, an improved echocardiographic image is produced.

Esophageal probes which combine an ECG component and echo producing transducer are known.

U.S. Pat. No. 4,319,580 to Colley and Martin discloses a method for detecting air emboli in the blood in an intracorpreal blood vessel using an esophageal catheter having a means adjacent the tip of the catheter for providing an ECG signal and also is provided with an ultrasonic transducer. A pulsed Doppler circuit energizes the transducer and provides a Doppler signal from return signals generated by the transducer as a result of returns of transmitted ultrasonic energy. A circuit processes the Doppler signal to obtain various information useful in the diagnosis. In use a intravascular catheter is positioned within a desired blood vessel after percutaneous insertion, and the esophageal catheter is positioned within the esophagus below the bifurcation of the trachea.

U.S. Pat. No. 5,178,149 pertains to a transesophageal echocardiographic probe having simultaneous cardiac pacing and echocardiographic capability. The probe comprises an echo producing transducer at the distal end of the probe and a pacing electrode located a selected distance up the distal end of the probe. The pacing electrode is located at a selected distance, i.e., about ten centimeters toward the proximal end of the probe from the transducer to provide optimal pacing and echocardiographic results.

This transesophageal probe will enable the device to electrically stimulate one heart chamber, such as the atrium, and at the same time image the heart through a different chamber, such as the ventricle, but not simultaneously from the same location or chamber. In addition, the device described does not enable electrocardiographic localization of the EKG signal. Moreover, the probe does not disclose that both the EKG electrodes and the echo producing means get in simultaneous contact with the wall of the esophagus or stomach without additional maneuvering of the device. Thus, different maneuvering is required for an echo signal than an EKG signal due to the distance between the two different electrodes.

SUMMARY OF THE INVENTION

The invention relates to an esophageal probe having both electrocardiographic (EKG) components and echocardiographic (ECHO) electrode components where the combined probe can be more easily and more precisely placed closer to the selected organ, e.g., heart or lung which produces a more controlled stimulation and/or more accurate diagnostic data, which may be converted to images on an echographic screen. The invention includes a tubular flexible conduit which is sized and shaped for insertion past the patient's pharynx. The distal end of the conduit is inserted into the body and the proximal end connected to a monitoring device. Preferably, the ECHO electrodes are longitudinally fixed on the exterior of the conduit and selectively positioned on the exterior of the conduit between the longitudinal positions of the EKG electrodes. A pair of ECHO electrodes are placed symmetrically relative to each other so that the relative placement of one inherently places the other. It is important that the selected spacing between the electrodes is within five (5) centimeters.

In accordance with the present invention, an esophageal probe comprises:

a flexible elongated conduit having a proximal end and a distal end;

a first EKG electrode means positioned near said distal end;

a first ultrasonic transducer means positioned in selective spaced relationship to said first electrode means;

a second ultrasonic transducer electrode means positioned in selective spaced relationship to said first transducer means;

a second EKG electrode means positioned in spaced relationship to said second ultrasonic transducer means and spaced at a distance from the proximal end;

a said proximal end adapted for receiving the conductive pathways from each of the electrodes and transducers or junction for connection with an electrocardiological device.

It is an object of the present invention to provide a combined esophageal probe which provides simultaneous EKG and ECHO signals from the same location on the probe monitoring such data.

Another object of the present invention is to provide a combined esophageal probe which can be more easily and more precisely placed closer to the selected organ.

Yet another object is to provide a combined esophageal probe with the necessary flexibility which provides a means for obtaining ECG signals and ECHO signals which can be interpreted by echocardiographic imaging modality.

A further object of the present invention is to provide an esophageal probe wherein the ECG electrode means and the ECHO electrode means are capable of transmitting as well as receiving electrical impulses.

Other objects of the invention, along with numerous advantages and features of the present invention, will become readily apparent from the following description of the preferred embodiments described below, form the drawings which accompany this application, and from the appended claims.

DETAILED DESCRIPTION OF THE PREFERRED EMBODIMENTS

The invention relates to an esophageal probe comprising in combination an electrocardiographic electrodes and an echocardiographic electrode.

Figure 1:
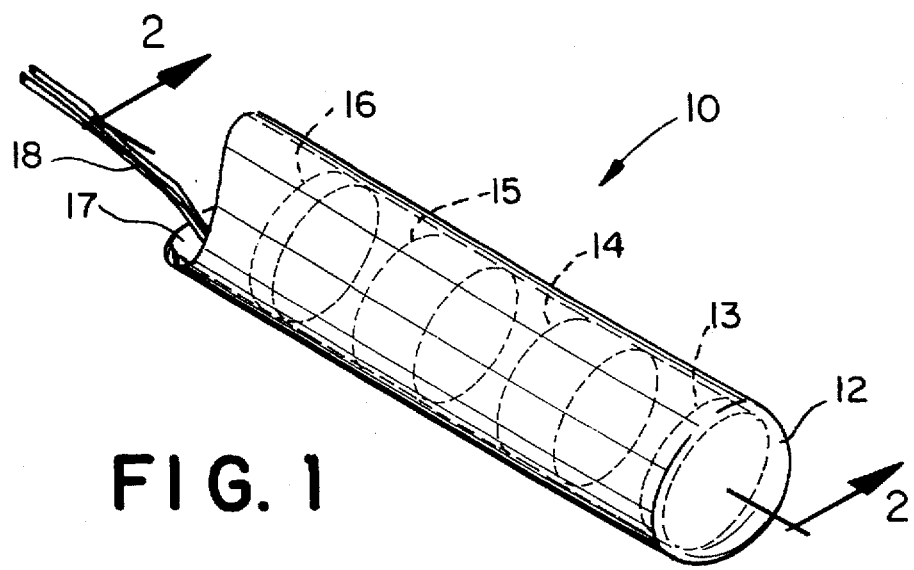
FIG. 1 is a top view of a combined EKG-ECHO esophageal probe of the invention.
Figure 2:
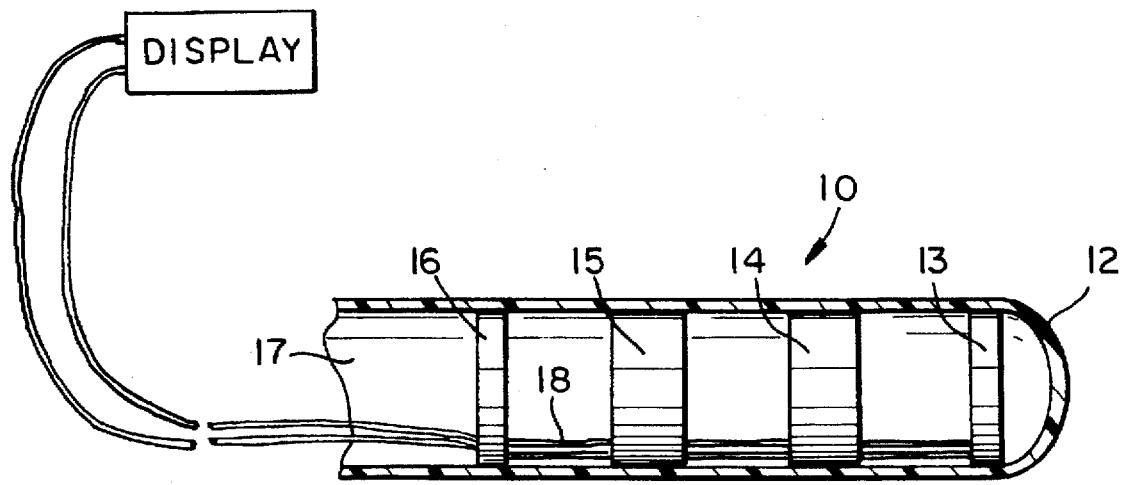
FIG. 2 is a side elevation view of a combined EKG-ECHO esophageal probe of the invention.

Referring to FIG. 1, there is presented a combination esophageal probe 10 constructed in accordance with the present invention. The probe 10 has a closed distal end 11 and a proximal end 14. A cylindrical conduit or tube 17 extends between the distal end 12 and the proximal end 14. The distal end 11 forms an integral part of the conduit 17 and has a hemispherical shape for insertion into the esophagus. The conduit 17 is made of biocompatible material and the electrodes are longitudinally positioned and spaced parallel to each other. In the preferred embodiment, the combination probe of the present invention is equipped with a first EKG or ECG electrode 13 at its distal end 12, Doppler ultrasound transducers electrodes 14 and 15 are interposed between a second EKG or ECG electrode 16. Each electrode component is selectively spaced at about five (5) centimeters center-to-center from each other on the specific pattern described around the circumference of the conduit 17. The proximal end 14 of the probe terminates into an interconnector (not shown) then to a monitoring device (not shown). The monitoring device processes the EKG signals and the Doppler signals to obtain various information in the diagnosis of the organ being examined. Such monitoring equipment is known to the art and commercially available.

The conduit 17 is tubular having a hollow interior to conduct heart sounds from inside the esophagus to the proximal end 14. The outside diameter of the conduit 17 is suitable for insertion past a patient's pharynx into the esophagus. In the preferred embodiment, the outer diameter is about 3 millimeters although conduits in the range of about 2.5 to 3.5 millimeters are useful. The conduit 17 is of thin walled construction, having an internal diameter of any suitable size for carrying conductive paths or leads on or through it to the proximal end 14.

In one preferred embodiment a first cylindrical distal EKG electrode 13 and a second cylindrical proximal EKG electrode 16 are circumferentially distributed around the conduit 17 at respective longitudinally spaced locations. Equal spacing between EKG electrode 13 and Doppler ultrasonic transducer 14, between Doppler ultrasonic transducer 14 and Doppler ultrasonic transducer 15 and between Doppler ultrasonic transducer 15, and between EKG electrode 16 is critical. It is also important that the distance between the electrodes is within five centimeters center-to-center to provide optimum organ stimulating means combined with localization of the echo data produced by the Doppler ultrasonic transducer resulting in improved echocardiographic data and imaging.

The EKG electrodes 13 and 16 are cylindrical rings made of electrically conductive medically inert material such as stainless steel, silver, or metallic paint. The diameter of these cylindrical rings of electrodes 13 and 16 is substantially equal to the diameter of the conduit 17, and may be slipped onto the exterior of the conduit 17 but will tightly bind to the exterior of the conduit so as to remain in position. It should also be understood that the electrodes could be fixed in location by other means, such as welding, soldering, adhered with conductive epoxy or by placement in a formed channel.

The Doppler ultrasonic transducers comprise an annular cylindrical ring of piezoeelectrical material having metallic conducting layers formed on its inner and outer cylindrical surfaces. The cylindrical ring is substantially equal to the inside diameter of the conduit. The Doppler ultrasonic transducers are coupled with a circuit which applies a high frequency electrical signal to a transmitting transducer to cause the transmission of ultrasonic energy in a fairly broad beam. Electrical output signals from the receiving transducer, resulting from the return signals of the transmitted ultrasonic energy from objects within the beam are compared with the high frequency electrical signal applied to the transmitting transducer to develop a Doppler signal representative of any frequency shift caused by the relative movement between an object and the probe. The Doppler signal is then amplified and converted to a monitor system which comprises a Doppler signal processor.

In a preferred embodiment, the Doppler ultrasonic transducers are used for both the transmission and reception of ultrasonic energy in order to meet the size constraints imposed upon the esophageal probe in order to simplify the detecting process.

In a preferred embodiment, Doppler ultrasonic transducers 14 and 15 transmit acoustic energy at ultrasonic frequencies, pause for a predetermined period and then receive signals echoed from the target zone. This pulsed Doppler mode is preferred over continuous wave Doppler mode. The pulsed Doppler mode is preferred over the continuous wave Doppler mode, particularly in a highly compact system designed for inserting into the body because the pulsed mode allows for a higher-frequency transducer requiring an inherently smaller crystal for generating the ultrasonic beam. Further, in pulsed Doppler mode, a single crystal acts sequentially, as both the transmitter and receiver avoiding the necessity of a second transducer and thereby reducing the size requirement of the probe device. Likewise, the pulsed Doppler mode requires less energy than the continuous wave Doppler mode. Such a reduction in energy requirements is highly desirable since it avoids undesirable cardiac reactions.

Several methods for making interconnection between the electrodes and the external monitoring or pacing equipment are available. A plurality of longitudinal conductive pathways, or leads (not shown) may be embedded in a recess in the wall of the conduit, on the exterior surface of the conduit on the interior surface of the conduit or in the lumen of the tube. Conductive pathways may be of identical cross-sectional area and may be selected from wire conductors, coaxial cable, and optical fibers. Any flexible electrically conductive material which is biocompatible may be used.

Fluid entry is blocked from entering the interior of the conduit 17 by appropriate fittings, closures, or fluid tight sealing techniques such as radio frequency (RF) welding.

The conduit 17 is long enough to permit positioning of the EKG electrodes 13 and 16, and ultrasonic transducers 14 and 15 in the esophagus closely adjacent to the heart of the patient. Healthy hearts make four characteristic sounds referred to as the first, second, third, and fourth cardiac sounds. The first and second sounds are the principle sounds. The first is deeper and longer and is caused by the contraction of the ventricles and the closure of the valves between the atria and the ventricles. The second sound is shorter and is caused by the closure of the valves between the ventricles and the two large arteries, i.e., the aorta and the pulmonary artery by which the blood leaves the ventricles. The third and fourth sounds are less audible. The sound is caused by the flow of blood into the ventricles. The fourth sound is caused by the contraction of the atria. By monitoring these cardiac impulses, the probe can be positioned along the length of the esophagus in the desired position relative to the specific heart chamber.

A normal electrocardiograph exhibits complexes which have been labelled as the P, QRS and T complexes of signals. The P wave corresponds to the depolarization of the atria. The QRS is the repolarization of the atrium and the depolarization of the ventricles. The T wave is the repolarization of the ventricles. When the same signals are monitored by a probe in the esophagus, the P wave is much greater relative to the QRS complex, which is indicative of placement near the atrium. Therefore, by connecting the probe in the esophagus to the monitoring equipment it is possible to place the probe at the position with the maximum measured P wave signal.

The longitudinal spacings of the ultrasonic transducers 14 and 15 and the EKG electrodes 13 and 16 are critical providing improved accuracy of monitoring heart parameters with optimum echocardiographic results. The EKG electrodes should be within five centimeters center-to-center of the ultrasonic transducer. This assures that adequate contact of the echo producing means will also provide adequate contact of the EKG electrode means at essentially the same location in the body.

At the commencement of the diagnosis procedure according to this invention, the throat of a fasted and sedated patient is sprayed with a local anesthetic such as a benzocaine or xylocaine spray to minimize the discomfort in the posterior pharynx. The patient is usually placed in the left lateral decubitus position to lessen the chance of aspiration of mouth secretions into the trachea. The patient's at-rest heart rate is measured and recorded. Continuous monitoring of the vital signs, transcutaneous oximetry and surface EKG is conducted. The distal end 11 of the combined probe 10 of this invention is then inserted into the esophagus and positioned where the atrium of the heart may be visualized on an echocardiography display screen. Two planes horizontal and verticle are produced if a biplanar probe is used. Multiple planes are obtained if an omniplanar transducer is employed. As mentioned hereinbefore, the echographic images are generated using existing technology, using piezo-electric crystals and a phased array echocardiographic probe that transmits suitable frequencies. Return signals generated by the ultrasonic transducer as a result of the reflected ultrasounds are transmitted by existing fiber optic technology to an echocardiographic machine such as the Hewlett-Packard, Series 1000 manufactured by Hewlett-Packard Corporation, sold under the trademark SONOS 2000 which converts the frequency data to an image display on the echocardiographic screen. Concurrently, the images may be recorded on video tape.

As the combined probe 10 of the invention approaches the atrium of the heart, a distinct EKG signal is displayed on the echocardiographic screen. The EKG signal shows a prominent P wave (an atrial activation wave form). As the probe is advanced further along the length of the esophagus, the EKG signal visualizes a prominent R wave (ventricular activation wave form) on the echocardiographic screen. As the probe continues to advance further, and although the echocardiographic signal may show little change, subtle movement of the probe may result in significant changes in the P-QRS-T morphology of the EKG signal obtained from the combined probe 10. The EKG signal is obtained from the contact of the EKG electrode with the esophagus which transmits the electrical impulses emanating from the heart through the EKG electrode to the echocardiographic machine and the EKG signal is displayed simultaneously on the video screen. Since more than one EKG electrode may be utilized, more than one signal may be simultaneously displayed on the video screen. Thus, EKG and ultrasonic signals are generated from the same location to provide a much improved and more accurate echocardiographic image.

In another embodiment, the combined probe 10 can be used to pace the heart to desired stress levels. At the onset of stress, emotion, exercise, or even in anticipation of these conditions in a person with a normal heart, the sympathetic nervous system response by constricting the interiors of central visceral and peripheral veins, increasing cardiac contractility and elevating heart rate. In some cases, the heart does not have the ability to raise the heart rate to allow for accurate diagnosis of coronary disease. The combined probe 10 of the present invention, through the EKG electrode components, may be positioned more precisely and proximate in relation to the specific chamber of the heart to provide an electrical pulse having a lower strength than normally required.

The close proximity to the heart chamber and the critical distance of the ultrasonic transducer 14 and 15, i.e., five centimeters center-to-center, from the EKG pacing electrode 13 and 16 requires less electrical energy and produces an improved echocardiographic image, since the ultrasonic transducers which receive the sonic output (atrial or ventricular wall motion of the stressed heart) may be positioned more accurately in a particular chamber.

It has been found that the shorter the distance between the ECHO and EKG elements, the more accurate is the correlation between the ECHO and EKG display, the better is the EKG location of the ECHO image, the less need for maneuvering the ECHO/EKG probe to obtain simultaneous ECHO and EKG signals from the same location within the body (such as esophagus, stomach, etc) or body surface in the case of transthoracic or other surface echocardiogram. The distance of less then 5 cm between ECHO and EKG components is therefore crucial since significant changes in signals may result in small changes of position of the probe in the esophagus.

It is envisioned that in versions of the combined probe in accordance with this invention, other esophageal functions such as: defibrillations, lung stimulation, and stomach diagnosis may be performed. Therefore, the invention should not be defined as limited to the preferred embodiment illustrated and described, but should be defined by the claims which follow:

What is claimed is:

1. An esophageal probe for use in diagnosis or as a stimulant comprising:

a flexible elongated conduit having a proximal end and a distal end;

a first EKG electrode positioned on said conduit near said distal end;

a first ultrasonic transducer longitudinally positioned on said conduit in selective spaced relationship to said first electrode;

a second ultrasonic transducer longitudinally positioned on said conduit in selective spaced relationship to said first transducer;

a second EKG electrode positioned on said conduit in selective spaced relationship to said second ultrasonic transducer and spaced at a distance from the proximal end;

the ultrasonic transducers being positioned between the EKG electrodes, conductive pathways connected to said electrodes and transducers;

said proximal end being adapted for receiving the conductive pathways from each of the electrodes and transducers for connection with electrocardiological and echocardiographic devices; and wherein the selective spaced relationship between each electrode and transducer is equal and not more than 5 centimeters.

2. The esophageal probe of claim 1 wherein each of said electrodes and each of said ultrasonic transducers are capable of transmitting and receiving electrical signals.

3. The esophageal probe of claim 1 wherein at least one EKG electrode is capable of cardiac stimulation.

4. The esophageal probe of claim 1 wherein the conductive pathways are wire conductors.

5. The esophageal probe of claim 1 wherein the conductive pathways are optical fibers.

6. The esophageal probe of claim 1 wherein each of said EKG electrode and said ultrasonic transducers are affixed around the exterior circumference of the conduit.

7. The esophageal probe of claim 1 where said first ultrasonic transducer emits ultrasonic waves which extend in all directions perpendicular to the surface of the transducer.

* * * * *